US008821585B2

(12) United States Patent
Pfeiffer et al.

(10) Patent No.: US 8,821,585 B2
(45) Date of Patent: Sep. 2, 2014

(54) COMPOSITE ANISOTROPIC TISSUE REINFORCING IMPLANTS HAVING ALIGNMENT MARKERS AND METHODS OF MANUFACTURING SAME

(75) Inventors: Ruth Pfeiffer, Hamburg (DE); Jörg Priewe, Keil (DE); Barbara Schuldt-Hempe, Bad Bramstedt (DE); Christoph Walther, Kattendorf (DE)

(73) Assignee: Ethicon, Inc., Somerville, NJ (US)

( * ) Notice: Subject to any disclaimer, the term of this patent is extended or adjusted under 35 U.S.C. 154(b) by 270 days.

(21) Appl. No.: 12/815,275

(22) Filed: Jun. 14, 2010

(65) Prior Publication Data

US 2011/0307077 A1 Dec. 15, 2011

(51) Int. Cl.
*A61F 2/02* (2006.01)
*A61F 2/00* (2006.01)

(52) U.S. Cl.
CPC ....... *A61F 2/0063* (2013.01); *A61F 2250/0067* (2013.01); *A61F 2/0045* (2013.01); *A61F 2250/0031* (2013.01); *A61F 2250/0097* (2013.01)
USPC ...................................... 623/23.72

(58) Field of Classification Search
USPC ......... 606/151, 213; 623/13.11, 13.17, 13.18, 623/13.19, 13.2, 23.64, 23.65, 23.66, 23.71, 623/23.72, 23.74, 23.75
See application file for complete search history.

(56) References Cited

U.S. PATENT DOCUMENTS

| | | | |
|---|---|---|---|
| 5,368,602 A | 11/1994 | de la Torre | |
| 5,593,441 A | 1/1997 | Lichtenstein et al. | |
| 6,270,530 B1 | 8/2001 | Eldridge et al. | |
| 6,881,226 B2 | 4/2005 | Corbitt, Jr. et al. | |
| 6,921,412 B1 | 7/2005 | Black et al. | |
| 6,966,918 B1 | 11/2005 | Schuldt-Hempe et al. | |
| 7,083,644 B1 | 8/2006 | Moroni | |
| 7,407,480 B2 | 8/2008 | Staskin et al. | |
| 7,615,065 B2 | 11/2009 | Priewe et al. | |
| 2003/0100955 A1* | 5/2003 | Greenawalt et al. | 623/23.74 |
| 2005/0070829 A1* | 3/2005 | Therin et al. | 602/1 |
| 2005/0113849 A1 | 5/2005 | Popadiuk et al. | |
| 2005/0288691 A1 | 12/2005 | Leiboff | |
| 2006/0282103 A1 | 12/2006 | Fricke et al. | |
| 2007/0250147 A1* | 10/2007 | Walther et al. | 623/1.5 |
| 2007/0299542 A1 | 12/2007 | Mathisen et al. | |
| 2008/0147198 A1 | 6/2008 | Cherok et al. | |

(Continued)

FOREIGN PATENT DOCUMENTS

| | | |
|---|---|---|
| DE | 29512361 | 12/1995 |
| FR | 2864443 | 9/2006 |
| WO | 03037215 | 5/2003 |

(Continued)

*Primary Examiner* — Thomas McEvoy
(74) *Attorney, Agent, or Firm* — Doherty IP Law Group LLC

(57) ABSTRACT

A composite implant includes an anisotropic surgical mesh having more stretchability along a first axis and less stretchability along a second axis that traverses the first axis, and an alignment marker overlying a first major surface of the anisotropic mesh and extending along the first axis. The implant includes a first absorbable, anti-adhesion film overlying the alignment marker and the first major surface of the anisotropic mesh, and a second absorbable, anti-adhesion film overlying the second major surface of the biocompatible mesh. The alignment marker is disposed between the first and second absorbable films and the first and second absorbable films are laminated to the anisotropic mesh.

17 Claims, 6 Drawing Sheets

(56) References Cited

U.S. PATENT DOCUMENTS

| | | |
|---|---|---|
| 2009/0149875 A1 | 6/2009 | Abele et al. |
| 2009/0152766 A1* | 6/2009 | Rousseau et al. ............. 264/241 |
| 2009/0216338 A1 | 8/2009 | Gingras et al. |
| 2009/0228021 A1 | 9/2009 | Leung |

FOREIGN PATENT DOCUMENTS

| | | | | |
|---|---|---|---|---|
| WO | 03041613 | | 5/2003 | |
| WO | 2007050382 | | 5/2007 | |
| WO | WO 2007/109062 | * | 9/2007 | ................ A61F 2/30 |
| WO | WO 2010/093333 | * | 8/2010 | ................ A61F 2/02 |

* cited by examiner

COMPOSITE ANISOTROPIC TISSUE REINFORCING IMPLANTS HAVING ALIGNMENT MARKERS AND METHODS OF MANUFACTURING SAME

CROSS-REFERENCE TO RELATED APPLICATIONS

The present application is related to commonly assigned U.S. Design patent application Ser. No. 29/363,759, filed on even date herewith, the disclosure of which is hereby incorporated by reference herein.

BACKGROUND OF THE INVENTION

1. Field of the Invention

The present invention generally relates to medical implants, and more specifically relates to tissue reinforcing implants.

2. Description of the Related Art

The use of tissue reinforcing implants, such as polymer meshes, is widespread. In 1995, a procedure was developed by F. Ugahary that combines the advantages of pre-peritoneal mesh fixation with the convenience of using small incisions for forming access openings.

Laparoscopic techniques have been developed for repairing inguinal hernias. One technique uses a trans-abdominal pre-peritoneal mesh-plasty (TAPP), whereby an implant mesh is preperitoneally positioned through a trans-abdominal laparoscopic access opening. Another technique is totally extra-peritoneal pre-peritoneal mesh-plasty (TEP), in which a large mesh is laparoscopically applied via an extra-peritoneal access opening. The implanted mesh covers all three potential hernia openings. Often, after the intraperitoneal implantation of polymer meshes, adhesions of internal structures occur, such as intestine, omentum, etc. Thus, there have been many efforts directed to providing implants that prevent, reduce the intensity of and/or minimize adhesions in the area of the implant, both in the center and in the periphery.

Tissue reinforcing implants, commonly referred to as areal implants, have been developed that match or compliment the mechanical properties of the underlying tissue. Orienting the areal implant relative to the underlying tissue may be important because both the target tissue and the implant have mechanical properties that are anisotropic. One example of an implant having anisotropic properties is a mesh with reinforcing fibers running in only one direction.

There are a number of problems associated with convention implants. For example, conventional implants may require surgeons to place alignment mark on the meshes for aligning the meshes on patients. The alignment marks are made using a skin marker that may easily wash off. In addition, after the implantation of polymer meshes, adhesions of internal structure often occur (e.g. intestine, omentum, etc).

Commonly assigned U.S. Pat. No. 7,615,065 to Priewe et al. discloses an areal implant that has a long-term, stable, mesh-like base structure with pores of a size in the range of 1.5 mm to 8 mm and is provided, at least in part, on both sides, with a synthetic, resorbable polymer film. The two polymer films are glued or welded together in the pores of the base structure. The implant disclosed in Priewe reduces the formation of adhesions of internal structures in human or animal organisms, and, after a period of time, facilitates tissue ingrowth.

WO 2003/037215 discloses an areal implant having a mesh-like basic structure, and an alignment marking in a central region that indicates the center of the implant. A marking line runs through the central marking. The central marking and the marking line running through the central marking are used for aligning the implant over a surgical opening for reinforcing the tissue.

In spite of the above advances, there remains a need for tissue reinforcing implants having anisotropic properties (e.g. elongation behavior) to simulate the anisotropic properties of the supported tissue (e.g. abdominal tissue). There also remains a need for tissue reinforcing implants that minimize or eliminate the occurrence of adhesions. In addition, there remains a need for tissue reinforcing implants having durable alignment markers. There also remains a need for tissue reinforcing implants that may be used for intra-peritoneal or laparoscopic applications, which fit through a trocar, that are simple to deploy, that may be fixable with sutures, tacks, or glues, and that have a mesh construction.

SUMMARY OF THE INVENTION

In one embodiment, a composite tissue reinforcing implant preferably includes a base component, such as a surgical mesh. In one embodiment, the surgical mesh preferably has anisotropic mechanical properties so that the mesh is more stretchable in a first direction and less stretchable in a second direction. In one embodiment, the composite implant preferably includes at least two absorbable, transparent films having a thickness of approximately 5-100 µm. The two absorbable transparent films are preferably laminated to the respective major faces of the surgical mesh. The absorbable films desirably have anti-adhesion properties. In one embodiment, the composite implant preferably includes an absorbable, polymeric marker including a center region disposable over the center of the implant, and two marking lines projecting from the center region. In one embodiment, the absorbable alignment marker is preferably shielded by the absorbable films and the surgical mesh so that the alignment marker remains stable during handling and surgery.

In one embodiment, the alignment marker is asymmetric and is desirably adapted to clearly show the center of the implant and the preferred placement direction for the implant. In one embodiment, the asymmetric alignment marker preferably includes two different marking lines running from a center region of the marker. The two marking lines preferably have different widths indicating the anisotropic elongation behavior of the surgical mesh. Outside the alignment marker region, the implant device is preferably transparent thereby allowing surgical personnel to see through the implant and observe critical structures such as underlying tissue, nerves and/or vessels.

In one embodiment, the composite implant disclosed herein may be used for repairing hernias, especially incisional hernias, particularly for intraperitoneal applications. In one embodiment, the composite implant may be positioned using laparoscopic techniques such as pelvic floor repair and for incontinence treatment.

In one embodiment, a composite implant preferably includes a tissue reinforcing film having a first major surface and a second major surface, an alignment marker overlying the first major surface of the tissue reinforcing film, and an absorbable film overlying the alignment marker and the first major surface of the tissue reinforcing film. In one embodiment, the alignment marker is preferably laminated between the absorbable film and the first major surface of the tissue reinforcing film.

In one embodiment, the tissue reinforcing film desirably includes a surgical mesh having pores extending between the first and second major surfaces thereof. In one embodiment, the surgical mesh preferably includes an anisotropic material adapted to have more stretch along a first axis and less stretch along a second axis that traverses the first axis. In one embodiment, the alignment marker desirably extends along the first axis of the implant for indicating the direction of the implant having more stretchability.

In one embodiment, the composite implant desirably includes a second absorbable film overlying the second major surface of the tissue reinforcing film. The second absorbable film is preferably laminated to the tissue reinforcing film and the first absorbable film. In one embodiment, the first and second absorbable films preferably have anti-adhesion properties, and at least one of the first and second absorbable films is transparent so that medical personnel may see the alignment marker and/or through the implant.

In one embodiment, the composite implant may include an adhesive film, such as a film made from polydioxanone (e.g. PDS film), disposed between the second absorbable film and the second major surface of the tissue reinforcing film for laminating the first and second absorbable films to the surgical mesh.

In one embodiment, the alignment marker preferably includes a central region adapted to be positioned at a center of the tissue reinforcing film, a first marking line extending from a first side of the central region of the alignment marker, and a second marking line aligned with the first marking line and extending from a second side of the central region of the alignment marker. The first and second marking lines are preferably aligned with the first axis of the anisotropic mesh.

In one embodiment, the first marking line preferably extends to a first end of the composite implant and the second marking line preferably extends to a second end of the composite implant. In one embodiment, the first and second marking lines have different widths, which may be used for distinguishing the different sectors of the implant for orienting the implant over tissue.

In one embodiment, a composite implant preferably includes an anisotropic mesh, such as a biocompatible, polymeric material, having more stretchability along a first axis and less stretchability along a second axis that traverses the first axis. The composite implant desirably includes an alignment marker overlying a first major surface of the anisotropic mesh and extending along the first axis. The implant preferably has a first absorbable, anti-adhesion film overlying the alignment marker and the first major surface of the anisotropic mesh, and a second absorbable, anti-adhesion film overlying the second major surface of the biocompatible mesh. The alignment marker is preferably disposed between the first and second absorbable films and the first and second absorbable films are laminated to the anisotropic mesh.

In one embodiment, the alignment marker preferably includes a polymeric film having a central region adapted to be positioned at a center of the anisotropic mesh, a first marking line extending from a first side of the central region of the alignment marker, and a second marking line extending from a second side of the central region of the alignment marker. The first and second marking lines are preferably aligned with the first axis of the implant. The first and second marking lines may have different widths.

In one embodiment, at least one of the absorbable, anti-adhesion films is transparent. In one embodiment, a PDS film may be disposed between the second absorbable, anti-adhesion film and the anisotropic mesh for facilitating lamination of the first and second absorbable, anti-adhesion films with the anisotropic mesh. In one embodiment, the anisotropic mesh desirably includes a polymeric mesh, the first and second absorbable, anti-adhesion films desirably include a MONOCRYL film, and the alignment marker preferably includes a PDS film.

In one embodiment, a method of making a composite implant includes assembling a pre-laminate structure having a surgical mesh having a first major surface and a second major surface, an alignment marker overlying the first major surface of the surgical mesh, a first absorbable, anti-adhesion film overlying the alignment marker and the first major surface of the surgical mesh, and a second absorbable, anti-adhesion film overlying the second major surface of the surgical mesh, whereby the alignment marker is disposed between the first and second absorbable films. In one embodiment, the method desirably includes applying pressure and heat to the pre-laminate structure to laminate the first and second absorbable films and the alignment marker to the surgical mesh.

In one embodiment, the applying pressure and heat step preferably includes applying pressure of about 4 N/cm$^2$-6.5 N/cm$^2$ to the assembled pre-laminate structure at a temperature of about 110-130° C. In one embodiment, the surgical mesh is desirably an anisotropic mesh having more stretchability along a first axis and less stretchability along a second axis that traverses the first axis. The alignment marker is preferably positioned over the surgical mesh so that it extends along the first axis.

In one embodiment, the composite implant includes a surgical mesh having anisotropic mechanical properties with elongation behavior. In one embodiment, after resorption of the resorbable parts of the implant (e.g. a resorbable film), the remaining mesh preferably shows a higher degree of stretch in a cranial to caudal (i.e. superior to inferior) direction than in a horizontal (i.e. lateral) direction so as to simulate the anisotropic behavior of the abdominal structures.

In one embodiment, the composite implant is preferably adapted to be folded for passing the implant through a trocar and then unfolded after passing from a distal end of the trocar. In one embodiment, prior to insertion through the trocar, the composite implant is preferably rolled up so that the marking lines of the alignment marker form the mid-axis of the implant. In one embodiment, the composite implant may be inserted through a trocar, and after deployment of the implant, the alignment marker including the marking lines are used for aligning the implant. In one embodiment, upon deployment of the implant, the marking lines preferably run from cranial to caudal. As such, after absorption of the absorbable films, there is a strained behavior in the implant in the desired orientation. As a result, the difficult process of intra-operative unfolding the implant with rotation by 90 degrees is avoided.

In one embodiment, the composite implant is preferably coated on both sides with an absorbable film. As such, it does not matter which side of the implant is positioned against an abdominal wall or intestine. This provides a clear advantage over other implants with only one side coated with collagen non-absorbable mesh such as Paritex or Parietene, or knitting structures with two different surface structures. One example of a commercial product having two different surface structures is sold under the trademark Dyna Mesh, which combines polypropylene (PP) and polyvinylidene fluoride (PVDF) monofilaments.

In one embodiment, a composite implant includes a long-term, stable, monofil basically flat, repair mesh having anisotropic elongation behavior. The composite implant preferably includes at least two synthetic absorbable, transparent films having a thickness from about 5-100 micrometers laminated on both side of the surgical mesh. The composite implant preferably includes an asymmetric, colored, absorbable, polymeric marker having a center region indicating the center of the implant, and two marking lines extending from the center region. The two marking lines desirably have different widths indicating the anisotropic elongation behavior of the implant. In one embodiment, the alignment markers are preferably oriented between the at least two synthetic absorbable films.

In one embodiment, one of the outer resorbable films is coated with a second or supplemental resorbable film, such as a PDS film. The second resorbable film desirably has the function of laminating the first and second outer resorbable films with the base component. The implant preferably includes an alignment marker that is laminated to the base component and that is covered by the two outer resorbable films. In one embodiment, the alignment marker is preferably an absorbable, colored film that is laminated between the first and second outer absorbable films. In one embodiment, gold or silver may be sputtered on the surface of the surgical mesh prior to lamination.

These and other preferred embodiments of the present invention will be described in more detail below.

DETAILED DESCRIPTION

Figure 1:
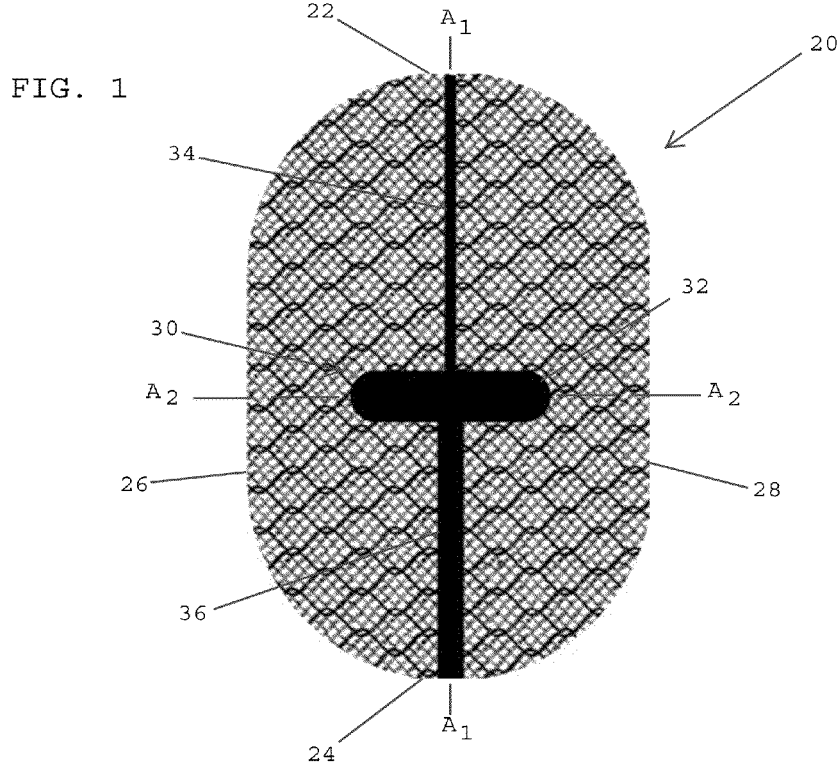
FIG. 1 shows a top plan view of a composite implant having an alignment marker, in accordance with one embodiment of the present invention.

Referring to FIG. 1, in one embodiment, a composite tissue reinforcing implant 20 preferably includes a first end 22, a second end 24, a first lateral side 26, and a second lateral side 28. The tissue reinforcing implant 20 desirably has an alignment marker 30 including a central region 32 that preferably indicates a center of the implant 20, a first marking line 34 that extends from the central region 32 of the alignment marker to the first end 22 of the implant 20, and a second marking line 36 that extends between the central region 32 of the alignment marker and the second end 24 of the implant 20. In one embodiment, the alignment marker preferably assists medical personnel in properly orienting and aligning the composite implant 20 over a patient's tissue so as to match the anisotropic properties of the implant with the anisotropic properties of the tissue.

Figure 2:
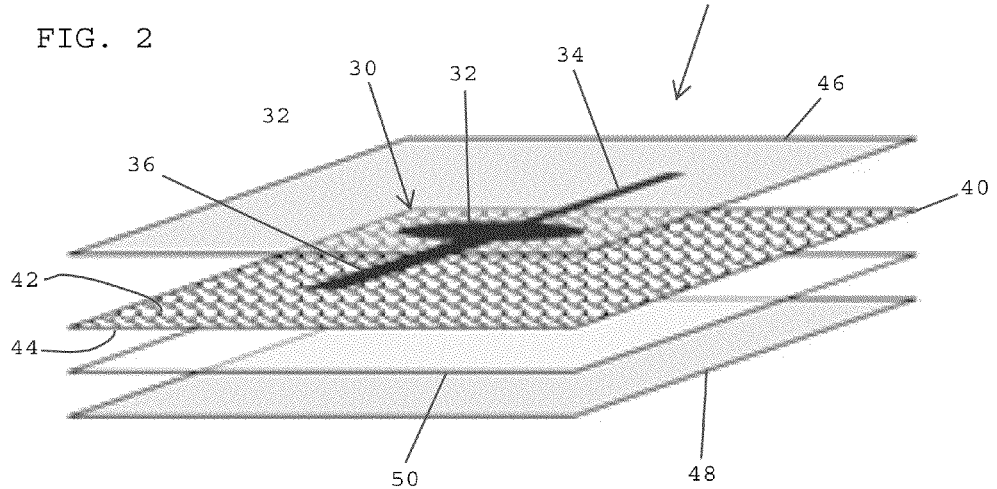
FIG. 2 shows an exploded view of the composite implant of FIG. 1.

Referring to FIGS. 1 and 2, in one embodiment, the tissue reinforcing implant is preferably a composite implant with layers or films that are laminated together. In one embodiment, the composite implant 20 preferably includes a surgical mesh 40 having a top major surface 42 and a bottom major surface 44. In one embodiment, the surgical mesh 40 has anisotropic properties so that the implant has more stretch along a longitudinal axis $A_1$ extending between the first and second ends 22, 24 of the implant 20, and less stretch along a transverse axis $A_2$ extending between the first and second lateral sides 26, 28 (see FIG. 1).

In one embodiment, the surgical mesh 40 is preferably a long-term stable base component that may be non-absorbable or slowly absorbable. As used herein, the terminology long-term, stable base component means a non-resorbable polymer or a very slowly resorbable polymer that desirably possess at least 50 percent of its original tearing strength 60 days after implantation. In one embodiment, the long-term, stable base component preferably includes substances such as polyamides, which are generally regarded as resistant and non-resorbable materials, and which may be exposed over time to body tissue and tissue fluids.

In one embodiment, the surgical mesh 40 may be made of one or more materials including polypropylene, mixtures of polyvinylidene fluoride, and/or copolymers of vinylidene fluoride, hexafluoropropene, polyglycolide-polylactide, or polyglecaprone (i.e., MONOCRYL film). In one embodiment, the surgical mesh 40 may be made from monofilaments, multifilament and/or threads having different diameters/sizes. In one embodiment, the surgical mesh 40 is desirably warp knitted.

In one embodiment, the surgical mesh preferably includes non-resorbable threads of polypropylene having a diameter of between about 0.089-0.13 mm, polyvinyllidene fluoride copolymer threads with a diameter of about 0.069-0.089 mm, PVDF threads with a diameter of about 0.089-0.13 mm, polyester threads with a diameter of about 0.08-0.12 mm and/or polyamide threads with a diameter of about 0.010-0.13 mm.

In one embodiment, the tissue reinforcing implant may be a surgical mesh product sold under the trademark ULTRA-PRO Partially Absorbable Lightweight Mesh (a/k/a ULTRA-PRO) used for what are commonly referred to as "open" hernia repair techniques. In one embodiment, the tissue reinforcing implant may be a composite structure that includes a surgical mesh, such as the composite structure sold under the trademark PROCEED Surgical Mesh, which may be used for hernia repair, especially for intraperitoneal applications and especially for laparoscopic applications. The PROCEED Surgical Mesh composite implant may be a multi-layer implant including oxidized regenerated cellulose (ORC) fabric, polydioxanone (PDS or PDO) film, polypropylene (PP) monofilament mesh (e.g. PROLENE mesh), and polydioxanone (PDS or PDO) film. During bending tests, both types of implants show an "anisotropic" behavior having higher bending stiffness in a wale direction and lower bending stiffness in a course direction. In one embodiment, the acronyms PDS and PDO mean polydioxanone or a polydioxanone film. In one embodiment, the term PROLENE mesh means a PROLENE Soft Polypropylene Mesh.

In one embodiment, the alignment marker 30 is preferably positioned over the first major surface 42 of the surgical mesh 40. In one embodiment, the central region 32 of the alignment marker is preferably centered over the first major surface 42 of the surgical mesh 40. As such, the central region 32 is preferably equidistant between the first and second ends 22, 24 of the surgical implant 20, and is also preferably equidistant between the first and second lateral sides 26, 28 of the implant 20. In one embodiment, the first marking line 34 preferably extends between the central region 32 of the alignment marker 30 and the first end 22 of the implant 20, and the second marking line 36 preferably extends between the central region 32 of the alignment marker 30 and the second end 24 of the implant 20. In one embodiment, the alignment marker 30 preferably extends along the longitudinal axis $A_1$ so that it differentiates between a "North-South" direction and an "East-West" direction.

In one embodiment, the alignment marker 30 may be made of a polymeric material. In one embodiment, the alignment marker 30 may be made of an absorbable material. The alignment marker 30 may have a color, such as violet. In one embodiment, the alignment marker 30 may have color differentiation for indicating the particular orientation such as a "north-south" direction and/or an "east-west" direction. The alignment marker may be an absorbable polymer material such as a PDS film.

In one embodiment, the alignment marker 30 preferably increases the bending stiffness of the composite implant 20 so as to facilitate unfurling and properly orienting the implant on a patient (e.g. orienting the implant in a "north-south" direction).

In one embodiment, the alignment marker desirably includes a coloring agent that preferably contains a dye and a binder such as a polymer. In one embodiment, printing or spraying techniques may be used to apply the alignment marker to a surgical mesh or an absorbable film. In one embodiment, the coloring agent may be prepared by dissolving dye and a polymer in a suitable solvent and spraying the alignment marker onto a base structure or one of the absorbable films using an air-brush technique or an ink-jet printer. After evaporation of the solvent, the desired markings are preferably firmly connected to the base structure or one of the absorbable films.

In one embodiment, the alignment marker is preferably at least partially absorbable and is preferably arranged between a surgical mesh and an absorbable film. In one embodiment, the alignment marker is a polydioxanone film having a thickness of approximately 150 μm. In one embodiment, the alignment marker is colored, such as a violet color. In one embodiment, the alignment marker may be cut from an extruded film sheet using common cutting techniques such as by using a laser, a knife, a cutting die, and/or ultrasound. In one embodiment, the alignment marker is preferably made from one piece of material, which facilitates positioning and orienting the alignment marker on an implant.

The composite implant 20 may be used for a broad range of surgical uses such as urethral support, pelvic floor support or hernia repair. Although the present invention is not limited by any particular theory of operation, it is believed that the alignment marker 30 enables surgical personnel to visually differentiate between the first and second ends and the lateral sides of the implant 20 so as to assist in properly orienting the implant relative to a patient. In one embodiment, the implant is anisotropic and the alignment marker enables surgical personnel to properly orient the implant to take advantage of the anisotropic properties of the implant for maximizing therapeutic benefit.

Referring to FIG. 2, in one embodiment, a first absorbable film 46 is secured over the first major surface 42 of the surgical mesh 40 with the alignment marker 30 positioned between the first absorbable film 46 and the surgical mesh 40. In one embodiment, the first absorbable film 46 is preferably laminated to the surgical mesh 40. In one embodiment, the first absorbable film is transparent so that the alignment marker 30 is visible through the first absorbable film 46. In one embodiment, the first absorbable film 46 is preferably adapted to resist the formation of tissue adhesions. In one embodiment, the composite implant 20 preferably includes a second absorbable film 48 having one or more of the properties of the first absorbable film 46. The second absorbable film 48 is preferably positioned over the second major surface 44 of the surgical mesh 40 for forming a laminated structure including the surgical mesh 40, the alignment marker 30 and the first absorbable film 46. In one embodiment, a film for facilitating lamination of the implant structure, such as a PDS film 50, may be disposed between the second absorbable film 48 and the second major surface 44 of the surgical mesh 40.

In one embodiment, the first and second absorbable films 46, 48 preferably have a thickness of between about 5-100 μm. The first and second absorbable films 46, 48 may be made from a synthetic absorbable material such as a laminate of MONOCRYL film and film made from polydioxanone (i.e., PDS film).

Referring to FIG. 2, in one embodiment, a process for forming a composite implant 20 preferably includes assembling a pre-laminate structure including the surgical mesh 40, the alignment marker 30 overlying the first major surface 42 of the surgical mesh 40, and the first and second absorbable films, 46, 48 overlying the respective first and second major surfaces 42, 44 of the surgical mesh 40. The alignment marker 30 is preferably disposed between the first absorbable film 46 and the first major surface 42 of the surgical mesh 40. In one embodiment, a polydioxanone film or PDS film 50 may be disposed between the second absorbable film 48 and the second major surface 44 of the surgical mesh 40. The pre-laminate structure is preferably disposed within a press adapted to apply pressure and temperature for a preferred period of time to sufficiently laminate and anneal the implant 20. In one embodiment, the pressure applied to the laminate structure is preferably about 5 N/cm² to about 6.5 N/cm². In one embodiment, the laminate structure is preferably exposed to a temperature of about 120° C. for between about 5-10 minutes. The laminated structure may be cooled while being held in position to avoid shrinkage of the implant 20.

In one embodiment, the composite implant 20 may be impregnated with a therapeutic agent such as a liquid-based therapeutic agent. More specifically, in one embodiment, the surgical mesh 40, the first absorbable film 46 and/or the second absorbable film 48 may be impregnated with a liquid based therapeutic agent such as Gentamicin, Octenidine, Polyhexamethylene Biguanide (PHMB), etc. The therapeutic agent may be incorporated into the surgical mesh 40, the first absorbable film 46, and/or the second absorbable film 48 using either horizontal or vertical dipping techniques.

In one embodiment, the composite implant 20 may include an active agent such as an antimicrobial agent. In one embodiment, a composite tissue supporting implant may include at least one biologically active agent that is preferably released locally after implantation. The biologically active agent may be applied to at least one of the layers of the composite implant, or just to a surgical mesh prior to lamination of the implant.

Substances which are suitable as active agents may be naturally occurring or synthetic and may include but are not limited to, for example, antibiotics, antimicrobials, antibacterials, antiseptics, chemotherapeutics, cytostatics, metastasis inhibitors, antideabetics, antimycotics, gynaecological agents, urological agents, anti-allergic agents, sexual hormones, secual hormone inhibitors, haemostyptics, hormones, peptide-hormones, antidepressants, vitamins such as Vitamin C, antihistamines, naked DNA, plasmid DNA, cationic DNA complexes, RNA, cell constituents, vaccines, cells occurring naturally in the body or genetically modified cells. The active agents may be present in an encapsulated form or in an absorbed form. With such active agents, the patient diagnosis can be improved according to the application or a therapeutic effect can be achieved (e.g., better wound healing, or inflammation inhibition or reduction).

In one embodiment, the active agents may be antibiotics including such agents as gentamicin or ZEVTERA™ (ceftobiprole medocaril) brand antibiotic (available from Basilea Pharmaceutica Ltd., Basel Switzerland). In one embodiment, an implant may include broad band antimicrobials used against different bacteria and yeast (even in the presence of bodily liquids) such as octenidine, octenidine dihydrochloride (available as active ingredient Octenisept® disinfectant from Schulke & Mayr, Norderstedt, Germany as), polyhexamethylene biguanide (PHMB) (available as active ingredient in Lavasept® from Braun, Switzerland), triclosan, copper (Cu), silver (Ag), nanosilver, gold (Au), selenium (Se), gallium (Ga), taurolidine, N-chlorotaurine, alcohol based antiseptics such as Listerine® mouthwash, N a-lauryl-L-arginine ethyl ester (LAE), myristamidopropyl dimethylamine (MAPD, available as an active ingredient in SCHERCODINE™ M), oleamidopropyl dimethylamine (OAPD, available as an active ingredient in SCHERCODINE™ O), and stearamidopropyl dimethylamine (SAPD, available as an active ingredient in SCHERCODINE™ S). In one embodiment, the agent may be octenidine dihydrochloride (hereinafter referred to as octenidine) and/or PHMB. The active agents may be applied together with an absorbable coating polymer to adjust the release time of the agents.

In one embodiment, a composite implant is impregnated with an antibiotic, antiseptic or therapeutic solution prior to implantation, preferably under operating room conditions. In one embodiment, the composite implant may be impregnated with the antibiotic, antiseptic or therapeutic solution by soaking the implant in a solution for up to five (5) minutes or more so as to impregnate the outer absorbable films and the inner surgical mesh. In one embodiment, a composite implant has dimensions of 7.5 cm by 15 cm and includes a 150 µm thick violet PDS film for an alignment marker. The alignment marker preferably includes a center marker section of about 10 mm in height and 20 mm in width, a north direction marking line with a width of about 3 mm and a south direction marking line with a width of about 5 mm. Both of the marking lines preferably run from the center section to the respective north/south edges of the implant. In one embodiment, the composite implant is preferably placed horizontally in an antiseptic solution for about five minutes. In one embodiment, the antiseptic solution is approximately 500 ml of 0.2 percent Lavasept. The implant is preferably dipped under the liquid surface of the antiseptic solution and the implant may be gripped with forceps and shaken for eliminating any excess solution. In one embodiment, the absorbable film surfaces are instantly wetted, and a surgical mesh between the absorbable films will be slowly wetted from the edges by displacing the air with the antiseptic liquid around the periphery of the implant. In one embodiment, over 50 percent of the mesh area is impregnated with the antiseptic solution after five minutes.

In one embodiment, a composite implant may be impregnated by using a standard laboratory dip coater. In one embodiment, the composite implant may be dipped into a solution of Octenidine dihydrochloride in acetone/water for at least five minutes and pulled with a draw speed of about three mm/sec. Using the above-described process, the composite implant may be completely impregnated with the solution inside and outside except for the inside area of glowing spots welding the two absorbable films in the centers of the pores together.

Figure 3:
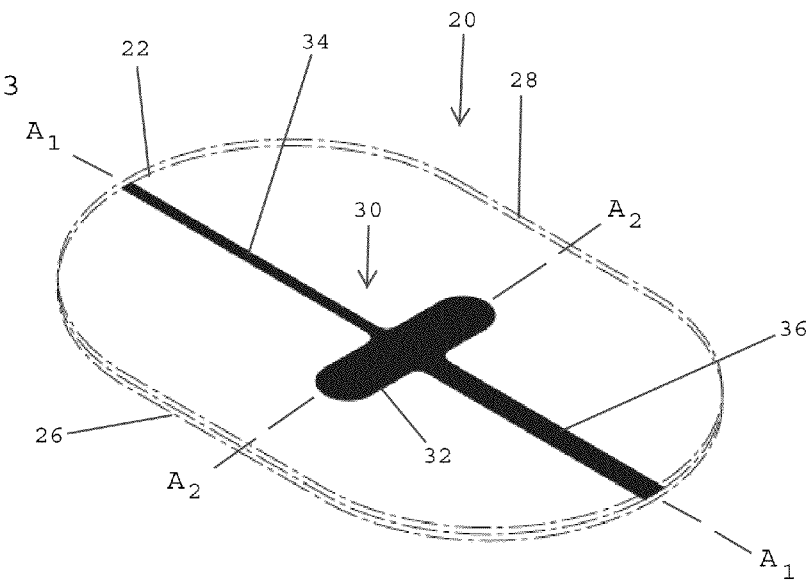
FIG. 3 shows a perspective view of a composite implant including an alignment marker, in accordance with one embodiment of the present invention.
Figure 4:
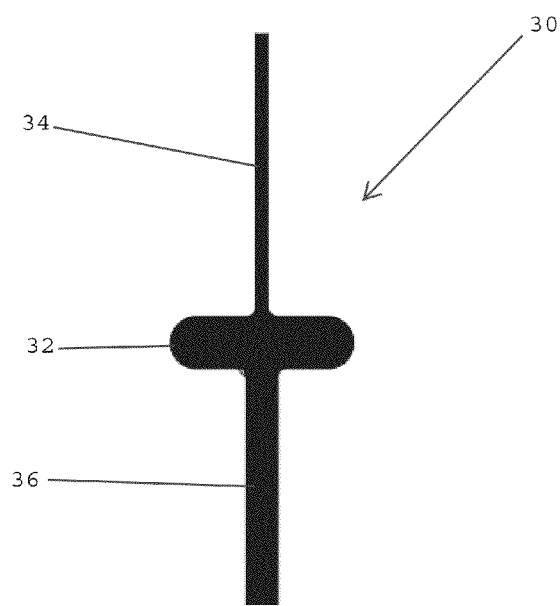
FIG. 4 shows a top plan view of the alignment marker shown in FIG. 3.

Referring to FIGS. 3 and 4, in one embodiment, the alignment marker 30 has at least one feature that enables surgical personnel to properly align the implant 20 on a patient. In one embodiment, the alignment marker is an asymmetric alignment marker that is laminated to the mesh 40 (FIG. 2) and that may be used by medical personnel for orienting the implant. In one embodiment, the asymmetric alignment marker 30 desirably includes a central region 32 that is preferably centered between the first end 22 and the second end 24 of the implant 20. In one embodiment, the central region 32 of the alignment marker 30 is preferably equidistant between the first lateral side 26 and the second lateral side 28 of the implant 20. The asymmetric alignment marker 30 desirably includes a first marking line 34 that extends between the central region 32 of the alignment marker 30 and the first end 22 of the implant 20. The alignment marker 30 preferably includes a second marking line 36 that extends between the central region 32 and the second end 24 of the implant 20. In one embodiment, the first marking line 34 and the second marking line 36 are preferably aligned with one another along an axis designated $A_1$. In one embodiment, the axis $A_1$ desirably defines a longitudinal axis of the implant 20. In one embodiment, the first marking line 34 preferably has a different width than the second marking line 36 so that medical personnel may properly distinguish the "North" and "South" ends of the implant for properly orienting the implant 20 over tissue. In one embodiment, the first marking line 34 is desirably narrower than the second marking line 36, which enables medical personnel to properly orient and align the implant 20 in a particular direction over a patient, such as a "North" direction.

In one embodiment, the surgical mesh 40 covered by the absorbable layers preferably has anisotropic properties so that the implant has more stretch in a first direction and less stretch in a second direction. Referring to FIG. 3, in one embodiment, the surgical mesh 40 is preferably adapted to be more stretchable along the longitudinal axis $A_1$ extending between the first and second ends of the implant and less stretchable along a transverse axis $A_2$ that extends between the first and second lateral sides 26, 28. The alignment marker 30 preferably enables surgeons to properly orient the implant 20 relative to tissue for maximizing the anisotropic properties of the implant. For example, some tissue regions of patients tend to stretch more in one direction than another direction, and tissue reinforcing implants with anisotropic mechanical properties may be implanted in a particular orientation in order to cooperate with the stretch characteristics of the underlying tissue.

FIGS. 1 and 3 show a composite implant having a generally oval shape. It is contemplated that the particular shape of a composite implant may be modified and still fall within the scope of the present invention. In other embodiments, a composite implant may have a circular, square, or rectangular shape.

Figure 5:
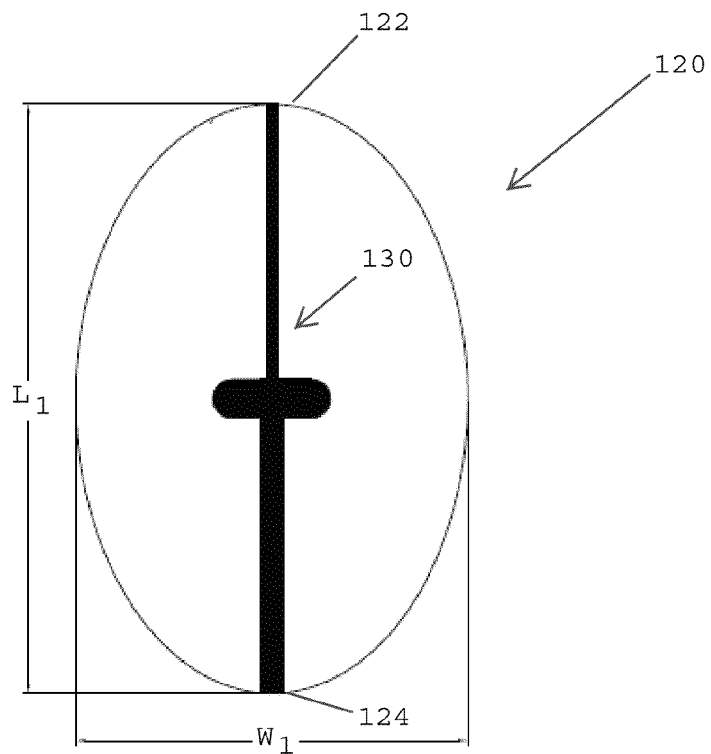
FIG. 5 shows a top plan view of a composite implant including an alignment marker, in accordance with one embodiment of the present invention.

Referring to FIG. 5, in one embodiment, a composite implant 120 has an elongated oval shape with a length $L_1$ of approximately 100-400 mm and a width $W_1$ of approximately 75-300 mm. An asymmetric alignment marker 130 desirably extends along a longitudinal axis of the implant, which preferably extends between a first end 122 and a second end 124 of the implant 120. The implant 120 preferably has anisotropic properties that enable the implant to have more stretch along the longitudinal axis of the implant and less stretch in lateral directions.

Figure 6:
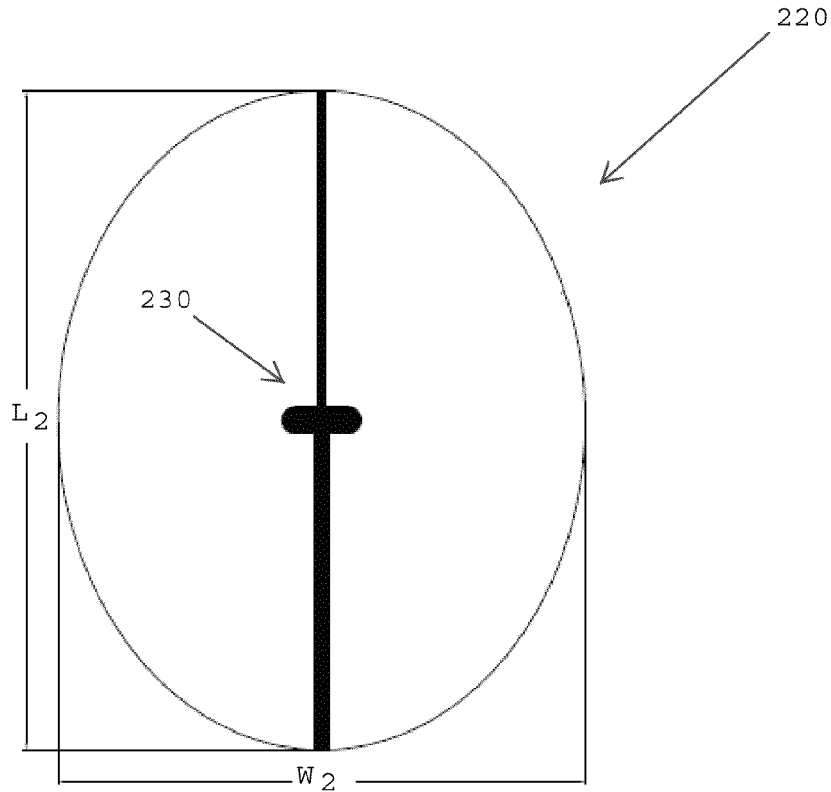
FIG. 6 shows a top plan view of a composite implant having an alignment marker, in accordance with one embodiment of the present invention.

Referring to FIG. 6, in one embodiment, a composite implant 220 has an oval shape, whereby the implant is wider than the implant shown in FIG. 5. In FIG. 6, the implant 220 preferably a length $L_2$ of approximately 200-300 mm and a width $W_2$ of approximately 150-200 mm.

Figure 7:
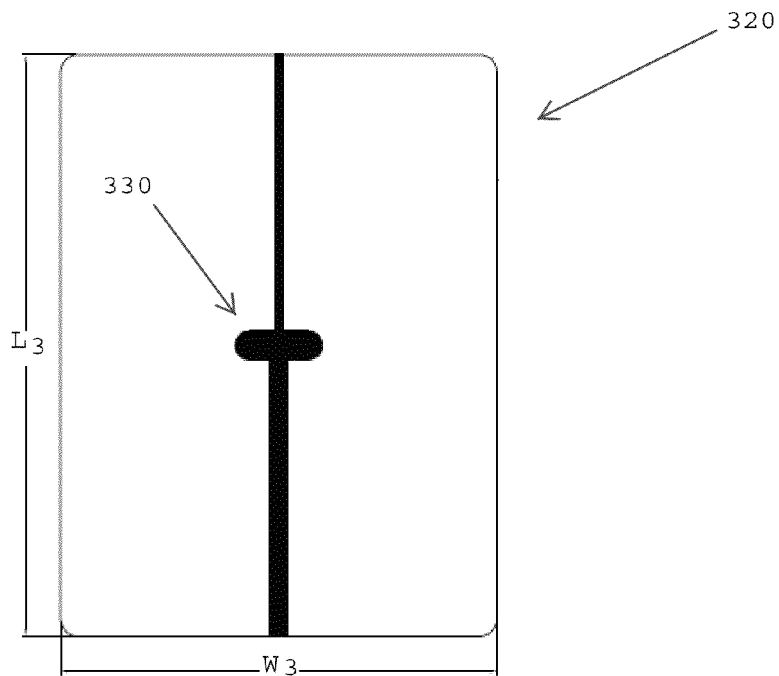
FIG. 7 shows a top plan view of a composite implant having an alignment marker, in accordance with one embodiment of the present invention.

FIG. 7 shows an embodiment whereby the implant 320 is rectangular, having a length $L_3$ of approximately 100-500 mm and a width $W_3$ of approximately 75-400 mm.

Figure 8:
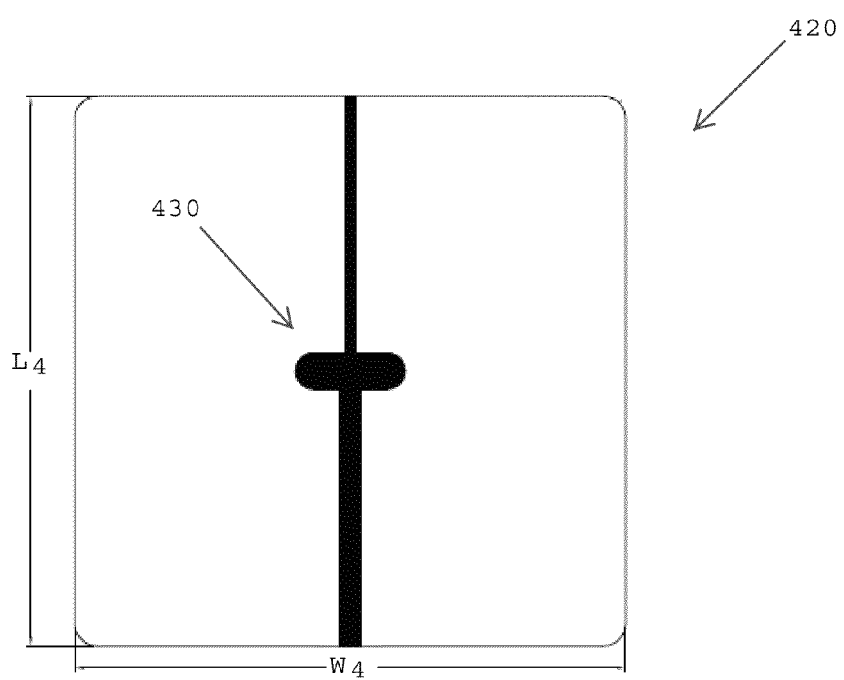
FIG. 8 shows a top plan view of a composite implant having an alignment marker, in accordance with one embodiment of the present invention.

FIG. 8 shows a composite implant 420 that is substantially square, having a length $L_4$ of approximately 100-400 mm and a width $W_4$ of approximately 100-400 mm. The embodiments shown in FIGS. 5-8 all desirably include an asymmetrical marker that enables surgical personnel to properly align the implant over tissue for reinforcing the tissue. In one embodiment, the implants have anisotropic properties, and the asymmetric markers preferably extend along an axis that identifies the direction of the implant having more stretchability and the transverse direction of the implant having less stretchability.

Figure 9:
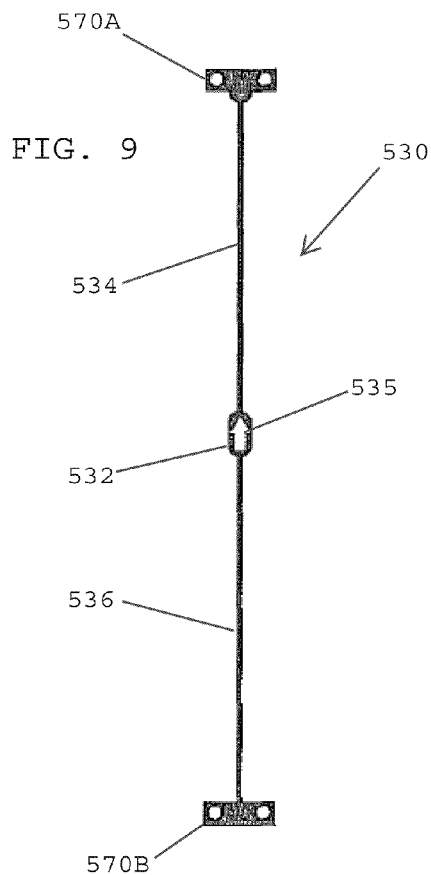
FIG. 9 shows a top plan view of an alignment marker for a tissue reinforcing implant, in accordance with one embodiment of the present invention.

Referring to FIG. 9, in one embodiment, an alignment marker 530 for a tissue reinforcing implant preferably includes a central region 532 that may be centrally located on an implant, such as the implant shown in FIGS. 1, 3 and 5-8 above. The alignment marker 530 preferably includes a first marking line 534 extendable toward a first end of an implant and a second marking line 536 extendable toward a second end of an implant. The alignment marker 530 may have an arrow 535 printed, cut and/or formed within the central region 532 to enable medical personnel to properly orient a surgical implant. In one embodiment, the alignment marker 530 is preferably positioned atop a major surface of a surgical mesh as shown in FIG. 2. The alignment marker 530 is preferably laminated to the surgical mesh. The first and second marking lines 534, 536 are preferably oriented with the axis of the implant having more stretch, which enables medical personnel to properly orient the implant.

Referring to FIG. 9, in one embodiment, the alignment marker is film having a thickness of about 100-200 μm and more preferably about 150 μm. In one embodiment, the alignment marker 530 is made from a colored PDS film. In one embodiment, the alignment marker 530 may include connecting members 570A, 570B having alignment openings provided at the outer ends of the respective first and second marking lines 534, 536. The connecting members 570A, 570B may be used during assembly of an implant for properly orienting the alignment marker 530 on the implant, and may be removed at a later stage of the assembly process to provide an implant having a final shape (e.g. the implant shapes shown in FIGS. 1, 3, and 5-8).

Figure 10:
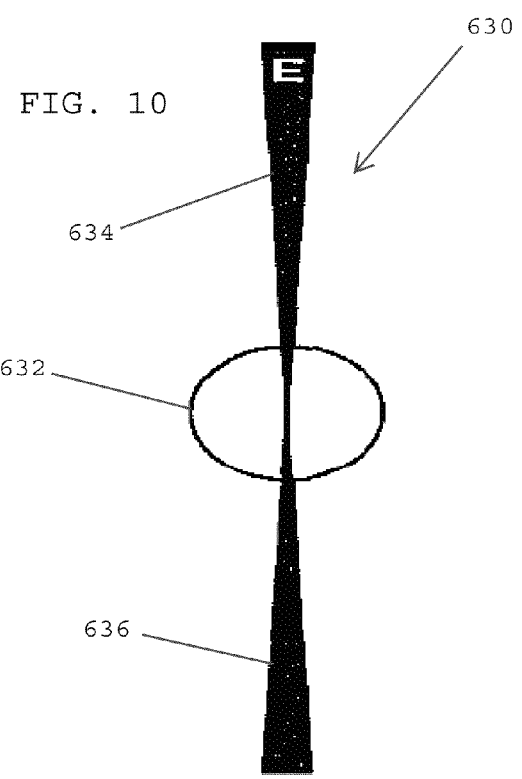
FIG. 10 shows a top plan view of an alignment marker for a tissue reinforcing implant, in accordance with one embodiment of the present invention.

Referring to FIG. 10, in one embodiment, an alignment marker 630 preferably includes a central region 632, a first marking line 634 extending from first side of the central region 632 and a second marking line 636 extending from an opposite side of the central region 632. In one embodiment, the central region 632 of the alignment marker 630 is preferably centered over a first major surface of a base component such as a surgical mesh. The first and second marking lines 634, 636 are preferably aligned with one another and may extend along an axis to indicate the anisotropic properties of the implant.

Figure 11:
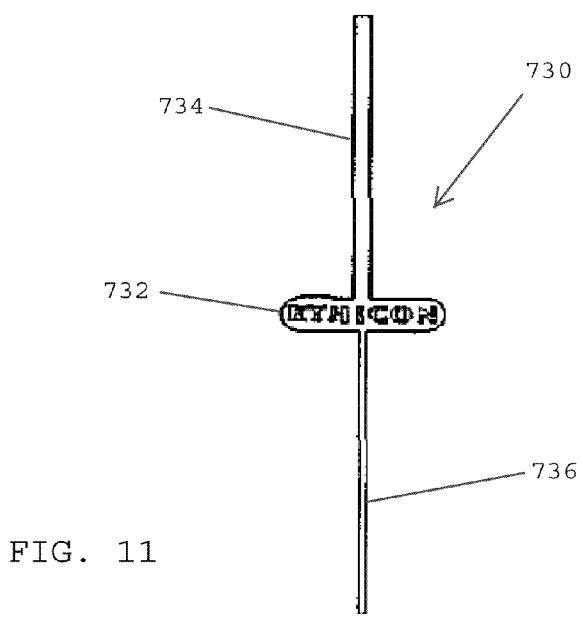
FIG. 11 shows a top plan view of an alignment marker for a tissue reinforcing implant, in accordance with one embodiment of the present invention.

Referring to FIG. 11, in one embodiment, an alignment marker 730 for a tissue reinforcing implant preferably includes a central region 732 that is adapted to be centered over a first major surface of a surgical mesh. The central region 732 may be centrally located between a first end and a second end of an implant, and between the first and second lateral sides of an implant, as shown in FIG. 1. The alignment marker 730 desirably includes a first marking line 734 that projects from a first side of the central region 732 and a second marking line 736 that projects from an opposite side of the central region 732. The first and second marking lines 734, 736 are preferably in alignment with one another along an axis. In one embodiment, the first marking line 734 preferably orients the implant so that the first making line 734 extends in a "North" or a "South" direction. In one embodiment, the first marking line 734 has a greater width than the second marking line 736.

Figure 12:
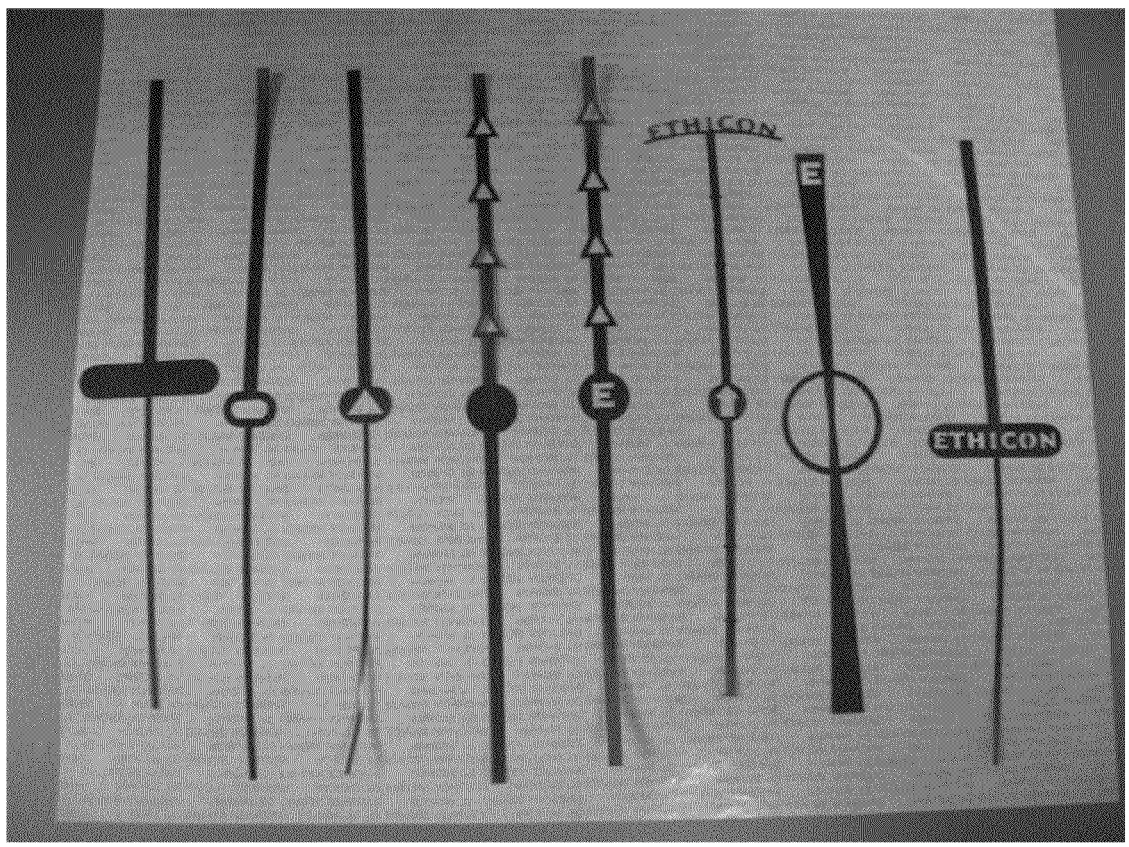
FIG. 12 shows alignment markers for tissue reinforcing implants, in accordance with embodiments of the present invention.

Referring to FIG. 12, in one embodiment, a plurality of alignment markers having different shapes and configurations may be used. The alignment markers are preferably positioned on a tissue supporting implant and laminated to the implant. The alignment markers are preferably used for properly orienting implants on a patient. In one embodiment, the implants have anisotropic mechanical properties and the alignment markers are oriented on the implants so that medical personnel may properly position the implants for taking advantage of the anisotropic properties of the implants.

Although the present invention is not limited by any particular theory of operation, it is believed that incorporating an alignment marker into a composite, laminated implant increases the stiffness of the implant, which improves the unfolding of the implant after dispensing the implant from a trocar or laparoscopic device.

In one embodiment, the alignment marker is disposed between an absorbable anti-adhesion film and a base component such as a surgical mesh. The absorbable film, the alignment marker, and the base component are preferably laminated together. The absorbable film and the base component desirably shield the alignment marker from external forces that may dislodge the alignment marker from the implant.

In one embodiment, the absorbable film is transparent so that the alignment marker is visible to medical personnel to aid the medical personnel is properly orienting the implant within a patient. In one embodiment, the base component and the alignment marker are laminated between a pair of transparent absorbable films that provide visibility of the alignment marker from both sides of the implant.

In one embodiment, a tissue reinforcing implant preferably includes a base component, such as a surgical mesh, an alignment marker overlying the base component, and a pair of outer absorbable films that are laminated over the base component and the alignment marker. A therapeutic agent is provided between the two outer absorbable films to provide good retention of the therapeutic agent by the implant prior to implantation.

In one embodiment, the alignment marker is asymmetric, which preferably provides visual differentiation between all four sides of an implant to assist in proper orientation of the implant within a patient.

In one embodiment, a process for forming a composite implant includes laminating and annealing the implant structure in a single step by constraining the implant structure in a press during the process, which provides for more efficient manufacturing of a composite implant.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A composite implant comprising:
   a tissue reinforcing film having a first major surface and a second major surface, said tissue reinforcing film having anisotropic properties so that said tissue reinforcing film is more stretchable along a first axis and less stretchable along a second axis that traverses the first axis;
   an asymmetric alignment marker overlying said first major surface of said tissue reinforcing film;
   an absorbable film overlying said alignment marker and said first major surface of said tissue reinforcing film, wherein said alignment marker is laminated between said absorbable film and said first major surface of said tissue reinforcing film, and
   wherein said asymmetric alignment marker includes first and second marking lines extending along the first axis for indicating the orientation of the more stretchable first axis and a central region positioned at a center of said tissue reinforcing implant and extending along the second axis for indicating the orientation of the less stretchable second axis, said first marking line extending from a first side of said central region, and said second marking line extending from a second side of said central region, said first and second marking lines having different widths for distinguishing a first end of said composite implant from a second end of said composite implant, and said central region of said asymmetric alignment marker having a width that is greater than the respective widths of said first and second marking lines.

2. The composite implant as claimed in claim 1, wherein said tissue reinforcing film is a surgical mesh having pores extending between said first and second major surfaces thereof.

3. The composite implant as claimed in claim 1, further comprising a second absorbable film overlying said second major surface of said tissue reinforcing film, wherein said second absorbable film is laminated to said tissue reinforcing film and said first absorbable film.

4. The composite implant as claimed in claim 3, wherein said first and second absorbable films have anti-adhesion properties, and wherein at least one of said first and second absorbable films is transparent.

5. The composite implant as claimed in claim 4, further comprising an adhesive film disposed between said second absorbable film and said second major surface of said tissue reinforcing film for laminating said first and second absorbable films together.

6. The composite implant as claimed in claim 5, wherein said adhesive film comprises a film made from polydioxanone.

7. The composite implant as claimed in claim 1, wherein said tissue reinforcing film having anisotropic properties comprises a flat, biocompatible, polymeric mesh, wherein said composite implant has an outer perimeter having an oval, circular, rectangular, or square shape, and wherein said tissue reinforcing film having anisotropic properties extends continuously from a center of said composite implant to the outer perimeter of said composite implant.

8. The composite implant as claimed in claim 1, wherein said first marking line has a width of about 3 mm, and said second marking line has a width of about 5 mm.

9. The composite implant as claimed in claim 1, wherein said composite implant has an outer perimeter having an oval, circular, rectangular, or square shape.

10. A composite implant comprising:
    an anisotropic mesh extending to an outer perimeter of said composite implant, said anisotropic mesh having anisotropic mechanical properties so that said composite implant is more stretchable along a first axis and less stretchable along a second axis that traverses the first axis;
    an asymmetric alignment marker overlying a first major surface of said anisotropic mesh and including first and second marking lines extending along the first axis for indicating the more stretchable first axis and a central region of said asymmetric alignment marker positioned at a center of said anisotropic mesh and extending along the second axis for indicating the less stretchable second axis, said first marking line extending from a first side of said central region, and said second marking line extending from a second side of said central region, said first and second marking lines having different widths for distinguishing a first end of said composite implant from a second end of said composite implant, and said central region having a width that is greater than the respective widths of said first and second marking lines;
    a first absorbable, anti-adhesion film overlying said alignment marker and said first major surface of said anisotropic mesh;
    a second absorbable, anti-adhesion film overlying said second major surface of said biocompatible mesh, wherein said alignment marker is disposed between said first and second absorbable films and said first and second absorbable films are laminated to said anisotropic mesh.

11. The composite implant as claimed in claim 10, wherein said anisotropic mesh comprises a flat, biocompatible, polymeric mesh having an outer perimeter that extends to and defines the outer perimeter of said composite implant.

12. The composite implant as claimed in claim 10, wherein said asymmetric alignment marker comprises a polymeric film.

13. The composite implant as claimed in claim 10, wherein said first marking line has a width of about 3 mm, and said second marking line has a width of about 5 mm.

14. The composite implant as claimed in claim 10, wherein at least one of said absorbable, anti-adhesion films is transparent.

15. The composite implant as claimed in claim 10, further comprising a film made from polydioxanone disposed between said second absorbable, anti-adhesion film and said anisotropic mesh for facilitating lamination of said first and second absorbable, anti-adhesion films with said anisotropic mesh.

16. The composite implant as claimed in claim 10, wherein said anisotropic mesh comprises a polymeric mesh having an outer perimeter that is coextensive with the outer perimeter of said composite implant, wherein said first and second absorbable, anti-adhesion films comprise MONOCRYL film, and wherein said alignment marker comprises colored PDS film.

17. The composite implant as claimed in claim 10, wherein said composite implant has an outer perimeter having an oval, circular, rectangular, or square shape.

\* \* \* \* \*